(12) United States Patent
Galili (10) Patent No.: US 6,613,330 B1
(45) Date of Patent: Sep. 2, 2003

(54) METHODS AND COMPOSITIONS FOR PREVENTING ANTI-GAL PRODUCTION IN XENOGRAFT RECIPIENTS

(75) Inventor: Uri Galili, Chicago, IL (US)

(73) Assignee: Rush University, Chicago, IL (US)

( * ) Notice: Subject to any disclaimer, the term of this patent is extended or adjusted under 35 U.S.C. 154(b) by 0 days.

(21) Appl. No.: 09/362,509

(22) Filed: Jul. 27, 1999

Related U.S. Application Data (60) Provisional application No. 60/096,062, filed on Aug. 11, 1998.

(51) Int. Cl.$^7$ .......................... A61K 39/44; C07K 14/00

(52) U.S. Cl. .................................... 424/183.1; 530/350

(58) Field of Search ................................ 435/110, 69.7, 435/183.1; 530/300, 350, 402

(56) References Cited

U.S. PATENT DOCUMENTS

| | | | |
|---|---|---|---|
| 4,305,720 A | 12/1981 | Bernstein | 23/230 B |
| 5,879,675 A | 3/1999 | Galili et al. | 424/93.1 |

FOREIGN PATENT DOCUMENTS

| | | |
|---|---|---|
| EP | 365087 | 4/1990 |
| WO | WO 95/24924 | 9/1995 |
| WO | WO98/33528 | 8/1998 |

OTHER PUBLICATIONS

Hertler et al. 1989. J. Clinical Oncology 17(2):1932–1942.*
Galili U, Rachmilewitz EA, Peleg A, Flechner I. A unique natural human IgG antibody with anti–alpha –galactosyl specificity. J. Exp. Med. 160:1519, 1984.
Galili, U, Clark MR, Shohet SB, Buehler J, Macher BA. Evolutionary relationship between the natural anti–Gal antibody and the Gal alpha–1,3Gal epitope in primates. Proc. Natl. Acad. Sci (USA) 84:1369, 1987.
Galili U, Anaraki F, Thall A, Hill–Black C, Radic M. One percent of human circulating B lymphocytes are capable of producing the natural anti–Gal antibody. Blood 82:2485, 1993.
Galili U, Macher BA, Buehler J, Shohet SB. Human natural anti–alpha–galactosyl IgG. II. The specific recognition of alpha (1,3)–linked galactose residues. J. Exp. Med. 162:573, 1985.
Galili U. Evolution and pathophysiology of the human natural anti–alpha–galactosyl IgG (anti–Gal) antibody. Springer Seminars in Immunopathology 15:155–171, 1993.
Galili U, Shohet SB, Kobrin E, Stults CLM, Macher BA. Man, apes, and Old World monkeys differ from other mammals in the expression of alpha–galactosyl epitopes on nucleated cells. J. Biol. Chem. 263:17755, 1988.
Lawson JH, Platt JL. Molecular barriers to xenotransplantation. Transplantation 62:303, 1996.

McCurry KR, Kooyman DL, Alvarado CG, Cotterel AH, Martin MJ, Logan JS, Platt JL. Human complement regulatory proteins protect swine–to–primate cardiac xenografts from humoral injury. Nature Medicine 1:423, 1995.
Galili U. Interaction of the natural anti–Gal antibody with alpha–galactosyl epitopes: A major obstacle for xenotransplantation in humans. Immunology Today 14:480, 1993.
Kozlowski T, Ierino F, Lombrigts D, Foley A, Andrews D, Awwad M, Monroy R, Cosimi AB, Cooper DKC, Sachs DH. Depletion of anti–Gal alpha–1–3Gal antibody in baboons by specific alpha–Gal immunoaffinity columns. Xenotransplantation 5:122, 1998.
Galili U, Minanov OP, Michler RE, Stone KR. High affinity anti–Gal immunoglobulin G in chronic rejection of xenografts. Xenotransplantation, 4:127, 1997.
Galili U, Tibell A, Samuelsson B, Rydberg L, Groth CG. Increased anti–Gal activity in diabetic patients transplanted with fetal porcine islet cell clusters. Transplantation 59:1549, 1995.
Galili U, LaTemple DC, Walgenbach AW, Stone KR. Porcine and bovine cartilage transplants in cynomolgus monkey: II. Changes in anti–Gal response during chronic rejection. Transplantation, 63:646, 1997.
Stone KR, Ayala G, Goldstein J, Hurst R, Walgenbach A,Galili U. Porcine cartilage transplants in cynomolgus monkey: III. Transplantation of alpha–galactosidase–treated porcine cartilage. Transplantation, 65:1577, 1998.
Lanzavecchia A. Receptor–mediated antigen uptake and its effect on antigen presentation to class II–restricted T lymphocytes. Annu. Rev. Immunol. 8: 773, 1990.
Vitetta ES, Fulton RJ, May RD, Till M, Uhr JW. Redesigning nature's poisons to create anti–tumor reagents. Science 238:1098, 1987.
Thrush GR, Lark LR, Clinchy BC, Vitetta ES. Immunotoxins: An update. Ann. Rev. Immunol. 14:49, 1996.

(List continued on next page.)

Primary Examiner—Karen Cochrane Carlson
(74) Attorney, Agent, or Firm—McDermott, Will & Emery (57) ABSTRACT

Toxin complexes and methods for preventing immune rejection of xenografts are provided. Cell toxins are coupled to carriers that display ligands which allow the complex to be recognized by antigen binding sites (i.e., specific B cell and T cell receptors) on the lymphocytes as the target cells responsible for the specific immune response. The toxin complexes interact with the specific receptors (antigen binding sites) on lymphocytes, and are internalized by these target cells. Once internalized, the toxin complex dissociates to release the cell toxin, which destroys the target cell. In one embodiment, the target cells are B lymphocytes and T lymphocytes, the antigen binding sites are anti-Gal B cell receptors and T cell receptors which interact with α-gal epitopes displayed on an α1-acid glycoprotein carrier. In other embodiments, the toxin complex is directed by the corresponding ligands to target cells responsible for autoimmune diseases in which the specificity of the autoantibodies is defined.

10 Claims, 4 Drawing Sheets

OTHER PUBLICATIONS

Vitetta ES, Thorpe PE, Uhr JW. Immunotoxins: magic bullets or misguided missiles? Immunol. Today 14: 252, 1993.

Thorpe PE, Ross WCJ, Cumber AJ, Hinson CA, Edwards DC, Davis AJS. Toxicity of diphtheria toxin for lymphoblastoid cells is increased by conjugation to antilymphocytic globulin. Nature 271:752, 1978.

Pirker R, FitzGerald DJP, Hamilton TC, Ozols RF, Willingham MC, Pastan I. Anti–transferrin receptor antibody linked to pseudomonas exotoxin as a model immunotoxin in human ovarian carcinoma cell lines. Cancer Res. 45:751, 1985.

Godal A, Fodstad O, Pihl A. Studies on the mechanism of action of abrin–9.2.27 immunotoxin in human melanoma cell lines. Cancer Res. 47:6243, 1987.

Scott Jr CF, Lambert JM, Goldmacher VS, Blattler WA, Sobel R, Schlossman SF, Benacerraf B. The pharmacokinetics and toxicity of murine monoclonal antibodies and of gelonin conjugates of these antibodies. Int. J. Immunopharm. 9:211, 1987.

Morgan Jr AC, Bordonaro J, Pearson JW, Sivam G. Immunotoxins to a human melanoma–associated antigen: resistance to pokeweed anti–viral protein conjugates in vitro. J. Natl. Cancer Inst. 78:1101, 1987.

Thorpe PE, Brown ANF, Bremner Jr JAG, Foxwell BMJ, Stirpe F. An immunotoxin composed of monoclonal anti–thy 1.1 antibody and a ribosome–inactivating protein from Saponaria officinalis: Potent antitumor effects in vitro and in vivo. J. Natl. Cancer Inst. 75:151, 1985.

Cumber AJ, Forrester JA, Foxwell BMJ, Ross WCJ, Thorpe PE. Preparation of antibody–toxin conjugates. Methods in Enzymology 112: 207, 1985.

Thorpe PE, Wallace PM, Knowles PP, Relf MG, Brown ANF, Watson GJ, Knyba RE, Wawrzynczak EJ, Blakey DC. New coupling agents for the synthesis of immunotoxins containing a hindered disulfide bond with improved stability in vivo. Cancer Res. 47: 5924, 1987.

pg,5

Thall, AD, Maly P, Lowe JB. Oocyte Gal alpha–1,3Gal epitopes implicated in sperm adhesion to the zone pellucida glycoprotein ZP3 are not required for fertilization in the mouse. J. Biol. Chem. 270: 21437, 1995.

LaTemple DC, Galiti U. Adult and neonatal anti–Gal response in knock–out mice for alpha–1,3galactosyltransferase. Xenotransplantation 5: 191,1998.

Yang Y–G, deGoma E, Ohdan H, Bracy JL, Xu Y, Iacomini J, Thall AD, Sykes M. Tolerization of anti–Gal alpha–1–3Gal natural antibody–forming B cells by induction of mixed chimerism. J. Exp. Med. 187: 1335, 1998.

Xu Y, Lorf T, Sablinksi T, Gianello P, Bailin M, Monroy R, Kozlowski T, Awwad M, Cooper DKC, Sachs DH. Removal of anti–porcine natural antibodies from human and non–human primate plasma in vitro and in vivo by a Gal alpha–1–3Gal beta–1–4–beta–Glc–X immunoaffinity column. Transplantation 65:172, 1998.

Galiti U. Anti–gal antibody prevents xenotransplantation. Science and Medicine, 5(5):28–37, 1998.

Galili U, La Temple DC. Natural anti–Gal antibody as a universal augmenter of autologous tumor vaccine immunogenicity. Viewpoint Immunology Today 18(6):281–285, 1997.

Schmid K, Burgi W, Collins JH, Nanno S. The Disulfide bonds alpha–1–acid Glycoprotein. Biochemistry 13(13):2694–2697, 1974.

Libert F, Lefort A, Gerard C, Parmentier M, Perret J, Ludgate M, Dumont JE, Vassart G. Cloning, sequencing and expression of the human thyrotropin (TSH) receptor: evidence for binding of autoantibodies. Biochemical and Biophysical Research Communications 165(3):1250–1255, 1989.

LaTemple DC, Henion TR, Anaraki F, Galili U. Synthesis of alpha–galactosyl epitopes by recombinant alpha–1,3galactosyltransferase for opsonization of human tumor cell vaccines by anti–galactose. Cancer Research 56: 3069–3074, 1996.

Joziasse DH, Shaper NL, Salyer LS, Van den Eijnden DH, van der Spoel AC, Shaper JH. Alpha–1,3galactosyltransferas: the use of recombinant enzyme for the synthesis of alpha–galactosylated glycoconjugates. Eur. J. Biochem 191:75–83, 1990.

International Search Report dated Oct. 7, 1999 for International Application No. PCT/US99/16993.

* cited by examiner

METHODS AND COMPOSITIONS FOR PREVENTING ANTI-GAL PRODUCTION IN XENOGRAFT RECIPIENTS

CROSS REFERENCE TO RELATED APPLICATIONS

This application claims priority to provisional application Ser. No. 60/096,062, filed Aug. 11, 1998, the disclosure of which is incorporated herein by reference.

FIELD OF INVENTION

The present invention relates to the field of organ and tissue xenotransplantation, and autoimmune diseases.

BACKGROUND OF THE INVENTION

The area of organ transplantation has been developed in the last 30 years to address the needs of many patients who suffer from organ failure and thus require a transplant of a functioning organ. Such human organs, termed allografts, are obtained from brain dead donors, or from family members in the case of kidney grafts. Nevertheless, more than 80% of patients in need of an organ such as heart, kidney, or liver fail to receive the allograft because of an insufficient number of organ donors. This shortage in allografts has prompted research for an alternative source of organs from other mammalian species. In particular, extensive research is being conducted on the use of tissue or organ grafts from other animal species, pigs in particular, (termed xenografts) for transplantation in humans. Transplantation of xenografts in humans or in monkeys was repeatedly found to result in rejection by a natural antibody. Galili and others have found that this rejection of xenografts is mediated by the interaction of the natural anti-Gal antibody, produced in humans, with α-gal epitopes (Galα1-3Galβ1-4GlcNAc-R, or Galα1-3Galβ1-3GlcNAc-R) on pig cells (Galili and Avila, α-gal and Anti-Gal, Subcellular Biochemistry Volume 32, New York: Kluwer Academic/Plenum Publishers, 1999).

Anti-Gal is a natural antibody that constitutes 1% of circulating immunoglobulins in humans, apes and Old World monkeys and can be produced by approximately 1% of B lymphocytes. By analyzing the specificity of this natural antibody, Galili et al. (Galili, et al., 1985, J. Exp. Med. 162:573; Galili, 1993, Springer Seminars in Immunopathology 15:155–171) found that anti-Gal interacts specifically with α-gal epitopes (termed in the literature also α-galactosyl epitopes or Gal α1-3Gal epitopes) on glycolipids and glycoproteins. They also found that the α-gal epitope is expressed as millions of epitopes per cell on various cells of nonprimate mammals, prosimians and New World monkeys (monkeys of South America) but not on cells of Old World Monkeys (monkeys of Asia and Africa, termed here as monkeys), apes and humans (Galili, et al.,1987 Proc. Natl. Acad. Sci (USA) 84:1369; Galili, et al., 1988, J. Biol. Chem. 263:17755). Transplantation of pig heart or kidney xenografts into monkeys was found to result in rejection within minutes. This rapid graft rejection, termed hyperacute rejection, is caused by the binding of natural anti-Gal IgM antibodies to the endothelial cells of the graft, activation of complement and lysis of these cells by activated complement components C7, C8 and C9 that form the membrane attack complex (MAC). This complex of activated complement molecules bores holes in the endothelial cell membrane (Lawson, et al., 1996, Transplantation 62:303). Concomitantly, this process induces platelet aggregation within blood vessels of the graft resulting in a rapid collapse of the vascular bed of the graft and ischemia, ultimately causing graft rejection (Lawson, et al., 1996, Transplantation 62:303).

Complement mediated hyperacute rejection of xenografts in monkeys suggested that xenograft rejection may be prevented by inhibition of complement activation. Recently grown transgenic pigs for human complement regulatory proteins, such as decay accelerating factor (DAF), have provided organs that do not activate complement upon binding of anti-Gal IgM molecules (McCurry et al., 1995, Nature Medicine 1:421.). Though no hyper acute rejection occurred with such organs, delayed rejection was observed within 24 hr (McCurry et al., 1995, Nature Medicine 1:421). This delayed xenograft rejection is largely mediated by the anti-Gal IgG molecules.

Anti-Gal IgG molecules are presently considered the major obstacle for success of xenotransplantation. This is because these IgG molecules mediate destruction of the xenograft cells by a process termed "antibody dependent cell mediated cytotoxicity" (ADCC) (Galili,1993, Immunology Today 14:480). In this process, killer cells with Fcγ receptors, such as granulocytes, monocytes, macrophages and natural killer (NK) cells, adhere to the Fc portion of anti-Gal IgG molecules on xenograft cells. The killer cells kill the xenograft cells by secreting their lytic enzymes into the contact area between the killer and target cell. Killing of xenograft cells by ADCC is a much slower process than complement mediated lysis of these cells. Nevertheless, this ADCC process effectively facilitates delayed and chronic xenograft rejection, i.e., rejection of the xenograft within days to weeks.

Removal of anti-Gal from the serum by plasmapheresis on immunoadsorbents can only delay xenograft rejection, since anti-Gal reappears within several days (Kozlowski et al., 1998 Xenotransplantation 5:122). Galili and coworkers (Galili et al., 1997, Xenotransplantation 4:127; Galili et al., 1995, Transplantation 59:1549; Galili et al., 1997, Transplantation, 63:646) reported that an even more serious problem for xenograft recipients is the major increase in production of high affinity anti-Gal as a result of the immune response to α-gal epitopes on the xenograft. The immune system in humans or monkeys transplanted with pig xenografts reacts against α-gal epitopes on the xenograft by producing large amounts of high affinity anti-Gal antibodies, primarily of the IgG isotype. These anti-Gal IgG molecules effectively induce chronic xenograft rejection, mainly by the mechanism of ADCC (Galili 1993, Immunology Today 14:480). The reason for this immune response in xenograft recipients is that B lymphocyte clones, which are capable of producing anti-Gal antibody molecules, interact via their specific B cell receptors, with the corresponding α-gal epitopes on glycoproteins of xenograft cell membranes. As a result of this interaction, these B lymphocyte clones are stimulated to proliferate, undergo isotype switch (i.e., convert from cells producing anti-Gal IgM molecules into cells producing anti-Gal IgG molecules) and undergo affinity maturation by somatic mutations (i.e., the immunoglobulin genes coding for anti-Gal gain mutations which increase the affinity of the antibody molecules to α-gal epitopes). Ultimately, these stimulated B lymphocytes in xenograft recipients differentiate into plasma cells producing large amounts of high affinity anti-Gal IgG antibody molecules in response to antigenic stimulation by α-gal epitopes on the xenograft. Galili and colleagues further showed that prevention of this stimulation of B lymphocytes in xenograft recipients can prevent most of the immune rejection process against the xenograft (Stone et al., 1998, Transplantation, 65:1577). They transplanted monkeys with pig cartilage that was enzymatically treated with recombinant α-galactosidase for the complete removal of α-gal epitopes. The cells in this cartilage were dead because of the treatment. The inflammatory reaction against such xenografts was marginal, whereas monkeys transplanted with untreated pig cartilage (i.e., cartilage expressing α-gal epitopes) displayed a massive inflammatory response (i.e., immune rejection) against the xenograft (Stone et al., 1998, Transplantation, 65:157).

Unfortunately, this enzymatic treatment is not applicable to xenografts containing live cells because the turn over of cell membranes results in the re-expression of α-gal epitopes on the treated cells. Another difficulty is that the production of high affinity anti-Gal in xenograft recipients can not be prevented by the immune suppression regimens used for prevention of allograft rejection. Galili et al. (Galili et al., 1995, Transplantation 59:1549) showed that patients transplanted with pig pancreas islet cells and with a human kidney allograft were induced to produced high affinity anti-Gal antibody molecules despite the massive immunosuppressive treatment, which was potent enough to prevent the rejection of the kidney allograft. All these studies imply that success of xenotransplantation is dependent on the effective prevention of the stimulation of the recipient's immune system by α-gal epitopes on the xenograft.

The described approach for preventing xenograft rejection may also be applicable to treating other disease states that are characterized by an overstimulation of the patient's immune system. Graves Disease is a thyroid disease characterized by an increased secretion of thyroid hormone caused by the body forming antibodies against thyroid stimulating hormone receptors. In Systemic Lupus Erythematosus (SLE) the body produces autoantibodies to DNA, RNA and nuclear proteins, resulting in vasculitis, arthritis, glomerulonephritis, and skin and other lesions. Effective treatments for these diseases are aimed at treating the symptoms of the disease, such as using anti-inflammatory drugs to reduce inflammation in SLE patients, or eliminating the thyroid gland in Graves Disease. Such measures fail to resolve the underlying causes of the diseases.

Hence, there is a need for new and effective therapies for limiting or preventing the immune system from attacking and rejecting xenografts and erroneously targeting the body's own tissues for destruction.

SUMMARY OF THE INVENTION

Figure 3:
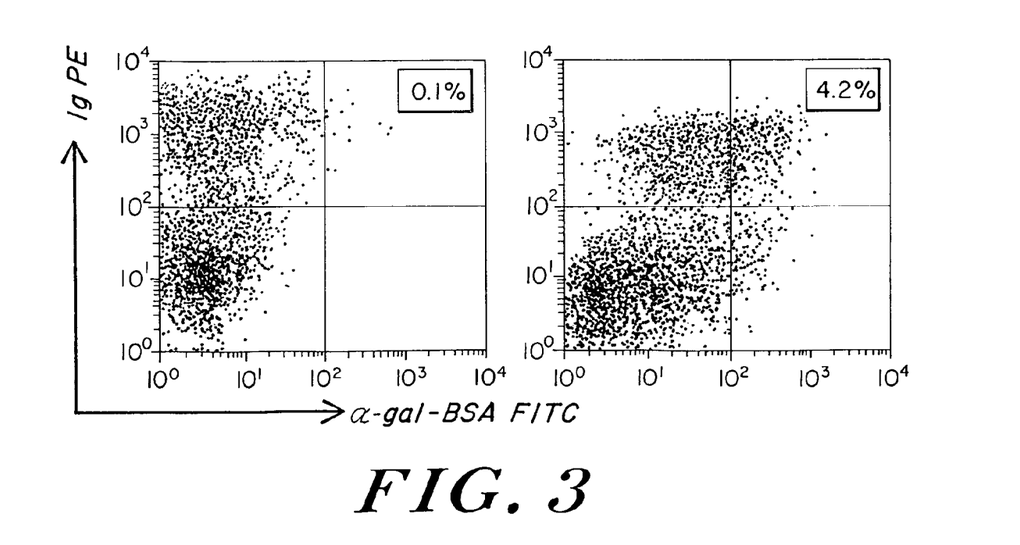

A toxin complex for the selective destruction of a population of target cells is provided. To form the toxin complex, a cytotoxic agent is associated with a carrier that displays a ligand capable of binding to antigen binding sites present on target cells. The target cells are B and T lymphocytes and the antigen binding sites are cell surface receptors, B cell receptors (BCR) and T cell receptors (TCR), respectively. In one aspect of the invention, the ligand is at least an antigen fragment, such as an epitope, that retains binding affinity to the antigen binding sites. In particular embodiments, the epitope can be the α-gal epitope and the antigen binding sites are anti-Gal antibodies as BCR, the epitope is DNA and the antigen binding sites are anti-DNA autoantibodies as BCR, or the epitope is thyroid stimulating hormone receptor (TSHR) and the antigen binding sites are anti-TSHR antibodies as BCR.

The cytotoxic agent can be any agent, that when internalized by the cell, causes cell death. It can be a radioisotope or, preferably, it is a plant or bacterially derived cell toxin, such as Ricin A, Diphtheria toxin, Pseudomonas exotoxin A, Abrin, gelonin, pokeweed antiviral protein, or saporin.

The carrier can be any macromolecule capable of being modified to display the ligand and be linked to the cytotoxin. It can be a naturally occurring macromolecule such as protein, glycoprotein, carbohydrates, oligosaccharide or polysaccharide, synthetic biopolymer or a chemically or enzymatically modified versions of any of the above. Specific embodiments of the carrier include human serum albumin, human α1-acid glycoprotein (orosomucoid), modified dextrans and starches, and poly-L-lysine. Specific embodiments of the complex include ricin A linked to an α1-acid glycoprotein carrier modified to replace the terminal sialic acids with α-gal epitopes, which functions as the ligand. This complex targets B lymphocytes presenting anti-Gal antibodies as B cell receptors and that are capable of producing anti-Gal antibodies, which cause rejection in xenograft transplants. A second embodiment of the complex includes DNA linked to human serum albumin as the carrier and Ricin A as the cytotoxin. This complex targets the anti-DNA autoantibodies responsible for the autoimmune disease SLE.

Another aspect of the invention provides a method for the destruction of a selected population of target cells by administering an amount of the toxin complex of the invention sufficient to kill the target cells. In one embodiment, the method uses a toxin complex wherein the carrier is a α1-acid glycoprotein modified to display the ligand α gal epitope, the target cells are B lymphocytes presenting anti-Gal antibodies as B cell receptors, and the cytotoxin can be either a plant or bacteria derived toxin or a radioisotope.

Yet another aspect of the invention provides a method for the inhibition of immune mediated xenograft rejection in an animal or human subject whereby the subject receives a therapeutically effective dose of the toxin complex which is compounded with one or more excipients for administration to the subject. In a preferred embodiment, the carrier is modified to display the ligand α-gal epitope, the target cells are B and T lymphocytes displaying the receptors that interact with this epitope.

Another aspect of the invention provides a method for the inhibition of autoimmune disease in an animal or human subject whereby the subject receives a therapeutically effective dose of the toxin complex which is compounded with one or more excipients for administration to the subject. In preferred embodiment, the ligand is thyroid stimulating hormone receptor, or DNA either of which is coupled to cytotoxin molecules.

BRIEF DESCRIPTION OF THE DRAWINGS

The foregoing and other objects of the this invention, the various features thereof, as well as the invention itself, may be more fully understood from the following description, when read together with accompanying drawings.

FIG. 1 shows a simplified biosynthetic pathway for the formation of the ligand α-gal epitope on a glycoprotein carrier of the invention. The terminal sialic acid from an N-linked carbohydrate chain is removed from the glycoprotein, exposing sites for the subsequent addition of galactose by recombinant α1,3-galactosyltransferase (r-α1,3-GT) onto the glycoprotein backbone.

FIG. 2 shows a graph showing anti-Gal IgG production in Knock Out mice (KO, i.e., knock out mice for the α1,3-galactosyltransferase gene). The KO mice were immunized three times (each in two week intervals) with 100 mg of pig kidney membranes (●), or they were non-immunized KO mice (○). Anti-Gal activity was measured by ELISA with α-gal-BSA (synthetic α-gal epitopes linked to bovine serum albumin) as solid phase antigen. Data represent anti-Gal activity in three characteristic mice of eight in each group with similar results.

FIG. 3 is a graph showing the identification of B lymphocytes with receptors for the α-gal epitope. Two color flow cytometry (in fluorescence activated cell sorter, FACS) analysis of B cells that interact with α-gal epitopes are shown in: (A) Non-immunized KO mice; (B) KO mice immunized with pig kidney membranes. The X-axis represents distribution of cells binding biotinylated α-gal-BSA and stained with FITC-avidin (i.e., B lymphocytes with membrane bound anti-Gal as the B cell receptor). The Y-axis represent distribution of cells binding phycoerythrin (PE) coupled goat anti-mouse Ig, i.e., cells that have membrane bound Ig molecules, a marker for B cells. The percentage of double positive cells is indicated in each figure. Data in each panel are from a characteristic mouse of seven mice with similar results.

Figure 4:
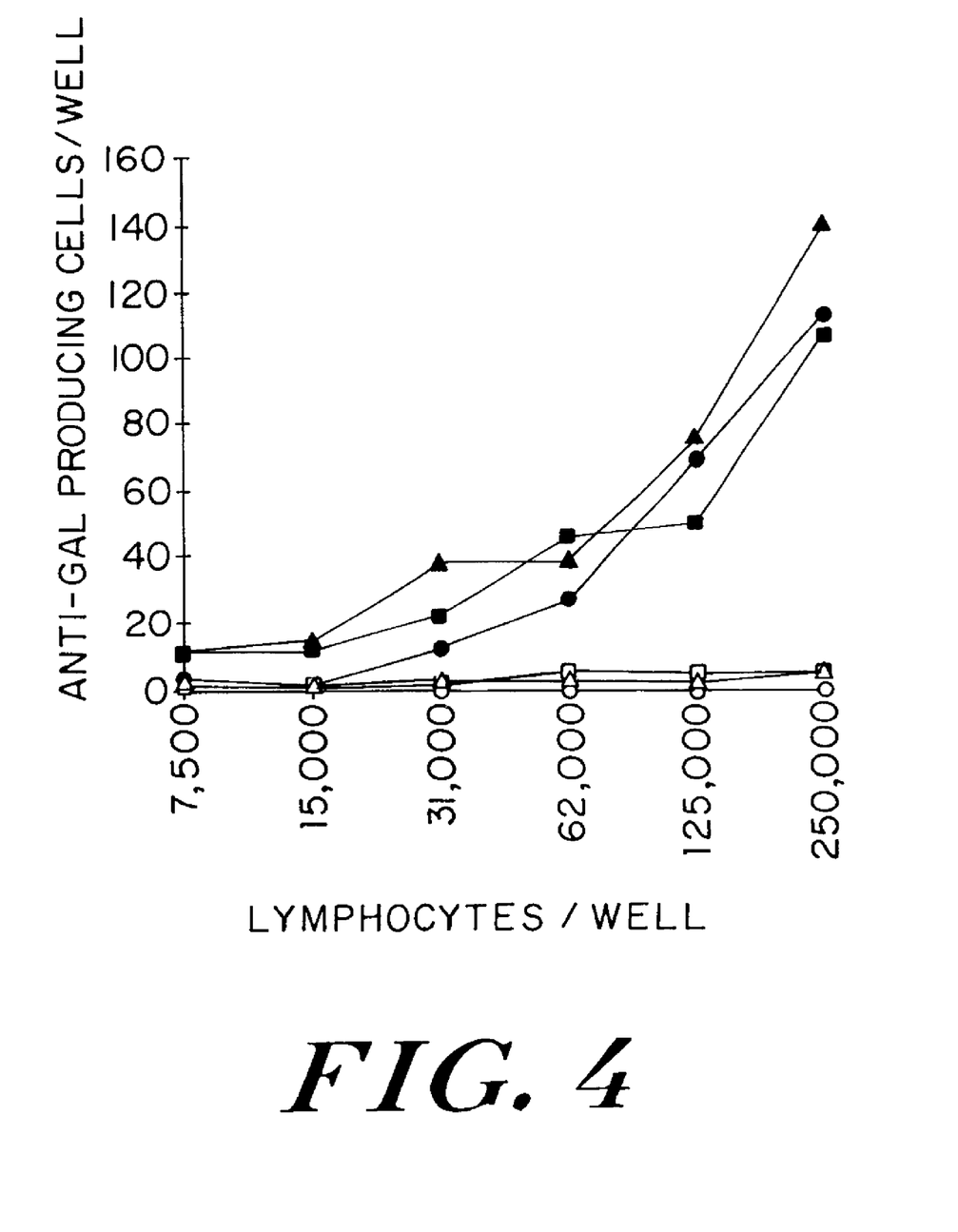

FIG. 4 is graph showing the identification of anti-Gal producing lymphocytes by ELISPOT. Anti-Gal producing lymphocytes from KO mice immunized with pig kidney membranes were assayed in ELISPOT wells. Spleen lymphocytes with receptors for α-gal epitopes were isolated by their binding to magnetic beads coated with this epitope and assayed for anti-Gal production. Lymphocytes that did not bind to the beads were assayed in parallel. Data are from three different mice (●, ○;; ■, □; ▲, △). Closed symbols represent anti-Gal producing cells in lymphocyte populations that bound the beads and open symbols represent anti-Gal producing cells in populations that did not bind the beads. Data are presented after subtraction on number of anti-Gal producing cells in ELISPOT wells coated with BSA.

Figure 5:
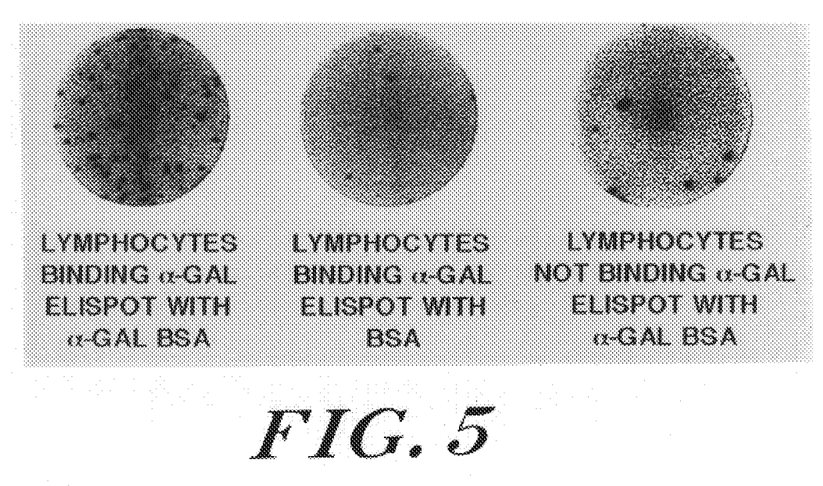

FIG. 5 represents a visualization of the ELISPOT assay data from one of the three mice in FIG. 4. The assay was performed with 250,000 spleen lymphocytes per well, incubated in wells coated with α-gal-BSA. Each dot represents an anti-Gal secreting B lymphocyte. Lymphocytes that bound to α-gal epitopes on the magnetic beads included many more anti-Gal producing cells than lymphocytes from the same spleen and which did not bind to the beads. The specificity of anti-Gal produced by the bead-bound lymphocytes is indicated by the finding that almost no spots are detected in the wells coated with BSA without the epitope.

DETAILED DESCRIPTION OF THE INVENTION

The present invention provides a composition and method that prevents overstimulation of the immune system in response to xenograft transplants or autoimmune dysfunction by targeting cell toxins to the cells responsible for the immune response. In this invention, the target cells are normal (i.e., non-transformed) B lymphocytes and T lymphocytes that express antigen binding sites for particular ligands. The antigen binding sites are membrane bound antibody molecules on B lymphocytes (B cell receptors) and T lymphocyte cell surface receptors (T cell receptors). These receptors normally bind antigens (the specific ligand for these receptors) and subsequently activate the lymphocytes to initiate an immune response. Targeting a cytotoxin to the target cell by way of antigen recognition and binding insures the specific destruction of the cells expressing the particular cell surface receptor, thereby eliminating the cause of the autoimmune disease or xenograft rejection.

In one embodiment, the ability of B lymphocytes to internalize the corresponding ligand that interacts with B cell receptors is exploited for specific destruction of B lymphocytes that are capable of producing anti-Gal that results in xenograft rejection. Anti-Gal producing B lymphocytes express on their cell membrane immunoglobulin molecules which have anti-Gal specificity (i.e., anti-Gal antibodies) and thus, they interact specifically with α-gal epitopes on xenograft cell membranes or on xenoglycoproteins and glycolipids. These anti-Gal molecules serve as the B cell receptors on anti-Gal producing B lymphocytes. The interaction of B cell receptors with the corresponding antigen results in the internalization of the antigen into the B lymphocyte (Lanzavecchia, 1990, Annu. Rev. Immunol. 8: 773). Within the B lymphocyte, the internalized antigen is processed and thereafter presented on the surface of the lymphocyte in association with Class II MHC (Major Histocompatibility Complex) molecules for the activation of helper T lymphocytes (Lanzavecchia, 1990, Annu. Rev. Immunol. 8: 773). Administration of cytotoxins coupled to carriers that display α-gal epitopes as ligands results in the specific binding of these complexes to membrane bound anti-Gal acting as B cell receptors on the B lymphocytes producing anti-Gal. The toxin complex is subsequently internalized, dissociates in the intracellular milieu, thereby releasing the free cytotoxin, which kills the cell. T lymphocytes, which have T cell receptors for α-gal epitopes, also bind the toxin complexes displaying the α-gal epitopes and are killed. Such treatment prevents anti-Gal production in xenograft recipients and thus, prevents immune rejection of the xenograft.

In a similar fashion, patients suffering from autoimmune disease can be treated with toxins coupled to ligands that interact with specifically with autoantibodies responsible for the autoimmune disease. The interaction of the toxin complex with the autoantibodies functioning as receptors on B lymphocytes, results in the specific selective destruction of the lymphocyte populations producing the autoantibodies. In Graves disease, antibodies to thyroid stimulating hormone receptor (TSHR, also termed thyrotropin receptor) continuously stimulate the thyroid gland to produce increased amounts of thyroglobulin and the thyroid hormones T3 and T4. The anti-TSHR antibody production can be prevented by administering a toxin complex in which a cell toxin is coupled to TSHR. These complexes bind to B cells with membrane bound anti-TSHR antibody molecules as B cell receptors. The complex molecules are internalized, dissociate to liberate the cytotoxin, and induce the death of lymphocytes that are capable of producing anti-TSHR.

For SLE, anti-DNA autoantibodies form immune complexes with DNA and cause inflammatory reactions in blood vessels, at various organs, including kidneys and brain. Production of these antibodies can be prevented by administering toxin complexes of DNA coupled to cell toxins. These complexes bind specifically to B cells with membrane bound anti-DNA antibodies as B cell receptors. Following this binding, the complex molecules are internalized in these B cells and induce the specific death of anti-DNA producing cells as described above.

The toxin complex is formed by linking a cell toxin to a carrier that displays the appropriate ligand. In this invention, the ligand is any molecule that can interacts specifically with B cell receptors or T cell receptors. In one embodiment, the ligand is an inherent part of the carrier itself, (for example, TSHR) where portions of the carrier molecule can bind to the antigen binding sites and other portions can couple to the toxin. In alternate embodiments, a carrier is modified to display one or more ligands. The ligand can be an antigen, an antigen mimetic, or any functional portion thereof that is capable of being recognized by the cell receptor and binding to it. An antigen mimetic is any molecule that mimics the recognition and binding of an antigen to the cell receptor.

The antigen mimetic may be a small molecule, carbohydrate, polysaccharide, peptide, or other molecule, that can bind to the B cell receptors and T cell receptors. By 'functional portion' is meant an antigen fragment or subunit, such as an epitope, (i.e, the smallest structural fragment on an antigen that can be recognized by a B cell or T cell receptor), or a hapten (i.e, an incomplete antigen that can interact with the receptor but does not induce an immune response unless complexed to a carrier). These ligands can be obtained commercially, purified from biological extracts, or be produced from recombinant, biochemical or synthetic methods. In the specific, non-limiting examples described below, several ligands are described, however, other combinations of ligands specifically interacting with B cell receptors or T cell receptors that are not detailed here are considered to be within the scope of the invention.

The preferred carrier is minimally immunogenic in humans and has sufficient functionality, either inherently, or can be so modified, to allow the attachment of the ligand and the toxin to it. Suitable carriers include, but are not limited to synthetic polymers, for example, poly-L-lysine, and naturally occurring polymers, such as polysaccharides, oligosaccharides, carbohydrates and derivatives thereof, for example, modified dextrans, hydroxyethyl starch and the like, and glycolipids, such as ceramide linked neolactoglycolipids. The most preferred carriers are human proteins such as human serum albumin (HSA), and preferably human α1-acid glycoprotein (also termed orosomucoid).

Carriers that display ligands are available commercially. For example, synthetic α-gal epitopes linked to human serum albumin or to bovine serum albumin are commercially available (Dextra Laboratories Ltd., Reading, UK). Other carriers may require some preparation before the attachment of the ligand. For example, some polysaccharides, such as dextran, may not naturally afford the reactive sites needed for the attachment of the ligand and must be derivatized, by methods well known in the art, to provide coupling sites for both ligands and toxins. Other carriers, such as HSA, need only to be modified with the ligand. Some molecules, such as TSHR can act as both carrier and ligand, and need no further preparation other than association with the cytotoxin.

Figure 1:
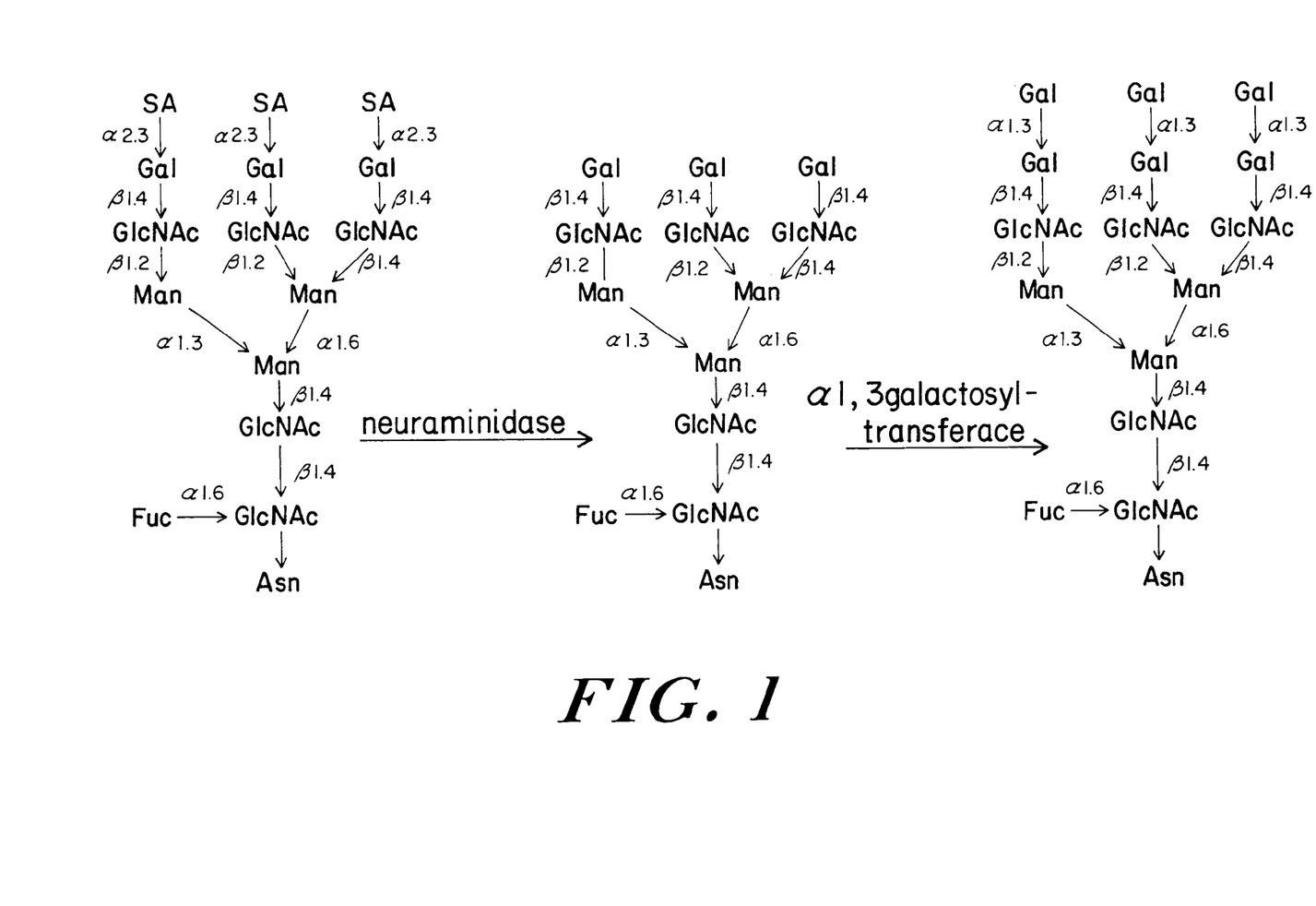

The human α1-acid glycoprotein is the preferred carrier. It is abundant in human serum and not immunogenic in humans. It can be obtained commercially, at reasonable and in purified form. α1-Acid glycoprotein is a small glycoprotein (m.w. 40,000) that has five N-linked carbohydrate chains, each with 2 or more antennae with the terminal structure SA-Galβ1-4GlcNAc-R (SA-sialic acid) (Schmid et al., 1973, Biochemistry 13:2694–2697). To synthesize the α-gal epitopes on this glycoprotein, the sialic acid is first removed to expose the penultimate N-acetyllactosamine (Galβ1-4GlcNAc-R). Next the appropriate carbohydrate is added to this backbone to synthesize the ligand. In the example reaction scheme shown in FIG. 1, neuraminidase is used to remove the terminal sialic acid; the α1-3Gal unit is added using a galactosyltransferase (here, recombinant α1,3 galactosyltransferase, or r-α1,3-GT) and uridine diphosphate-galactose (UDP-Gal) as the sugar donor (Joziasse et al., 1990, Eur. J. Biochem 191:75–83). Other methods for removing the terminal sialic acid and adding a ligand can be used, such as the chemical removal of the sialic acid as shown in Example 2.

The number of ligands that can be added to a carrier is carrier-specific. For example, HSA has binding sites (i.e., terminal amino groups on lysine residues) that can accept up to 25 synthetic α-gal epitopes; the human α1-acid-glycoprotein has 5 N-linked carbohydrate chains, which can accept up to 15 α-gal epitopes, can be synthesized on the exposed N-acetyllactosamine chains. Theoretically, only one ligand per carrier is needed for targeting the toxin, however, increasing the number of ligands per carrier may increase targeting efficiency. Similarly, adjusting the reaction conditions can influence the number of ligands that are added.

Suitable toxins include any agent that is capable of inducing cell death (cytotoxic agent or cytotoxin). Cell death can occur by disruption of cellular machinery, such as protein synthesis or changing the nature of the cell in a manner detrimental to the cell that ultimately causes its death. The preferred toxins used in this invention are derived from bacteria and plants, and are capable of effectively inhibiting protein synthesis within cells by inhibiting ADP-ribosylation of elongation factor 2, or by functioning as N-glycosidase for 28S ribosomal RNA. Such toxins can include Ricin, Diphtheria toxin, Pseudomonas exotoxin A, abrin, gelonin, pokeweed anti-viral protein, or saporin. These toxins are usually constructed of two sub-units termed chains A and B that linked to each other by a disulfide bond. In their natural state, chain B mediates the binding of the toxin to the target cell and the internalization of the toxin into the endosomal compartment, and chain A transfers from the endosomal compartment into the cytosol where it induces its cytotoxic effect. This transfer requires the cleavage of the disulfide bond between chains A and B which occurs under the reducing conditions in the endosomal compartment. However, most of these toxins are available commercially as chain A with a free thiol group as a result of the cleavage of the disulfide bond by reducing agents (Vitetta et al., 1987, Science 238:1098; Thruch et al., 1996, Ann. Rev. Immunol. 14:49; Vitetta et al.,1993, Immunol. Today 14: 252; Thorpe et al., 1978, Nature 271:7521; Pirker, 1985, Cancer Res. 45:751; Scott et al., 1987, Int. J. Immunopharm. 9:211; Morgan et al., 1987, J. Natl. Cancer Inst. 78:1101, Thorpe, 1985, J. Natl. Cancer Inst. 75:151; Cumber et al., Methods in Enzymology 112: 207, 1985). Other toxins include radioisotopes, such as Iodine$^{125}$, (I$^{125}$) and Iodine$^{131}$ (I$^{131}$) which are capable of killing the targeted cells by intracellular radiation upon internalization.

To complete the toxin complex, the toxin itself is associated with the carrier. This association may a physical association between the carrier and toxin molecule, as in, for example, a toxin-micelle complex in which micelles displaying the appropriate ligand surround a toxin molecule, for example a radioactive isotope. Alternatively, the toxin can be chemically linked to the carrier, either directly if the carrier affords suitable reactive sites, or more preferably through a linking agent, such as a heterobifunctional linking agent. The preferred method for forming the toxin complexes involves linking agents that couple the toxin to the carrier through a lysine or functionally similar group on the carrier to a free thiol on the toxin. This type of linkage is stable in plasma but readily dissociates within the reducing environment of the cell to release the free toxin. Such linking agents are available commercially, for example 4-succinimidyloxycarbonyl-methyl-α[2-pyridyldithio] tolune (SMPT, Pierce Inc. Rockford, Ill.), and N-succinimydyl 3-2(-pyridyldithio)propionate (SPDP, Molecular Biosciences, Boulder, Colo.). Others suitable for use with invention are detailed in the art, for example those used for linking monoclonal antibodies to toxins (For example: Thorpe et al., 1987, Cancer Research 47:5924–5931; Cumber et al., 1985, Methods in Enzymology, 122:207–225).

Since radioisotopes generally do not provide a free thiol group for linking to the carrier, they can be coupled to carriers such as proteins via standard iodination methods, for example, using Bolton-Hunter reagent to link the toxin to tyrosine groups on the protein.

Figure 2:
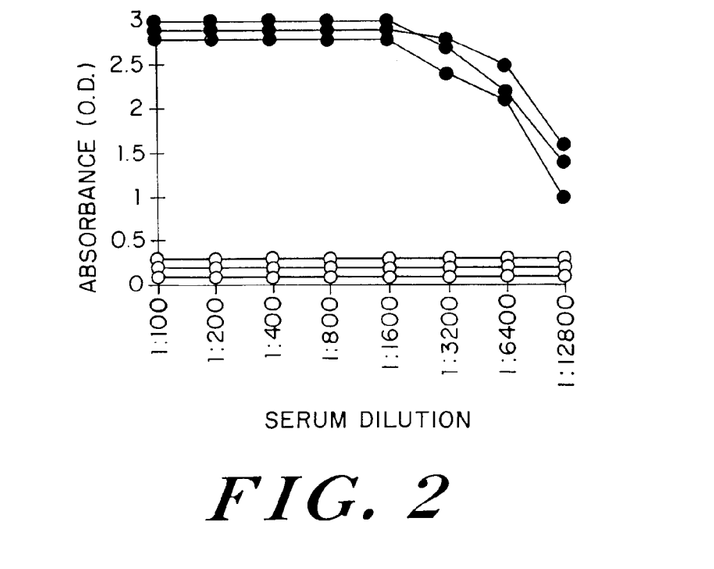

It has been shown that after the internalization of toxin molecules such as Ricin A, Diphtheria toxin, or Pseudomonas exotoxin A, it is sufficient for one toxin molecule per cell to reach the cytoplasm in order to destroy the protein synthesis machinery and to induce cell death. However, the toxin loading of the toxin complex (i.e., number of toxin molecules per carrier molecule) can be adjusted by appropriate reaction conditions or choice of carrier to increase or decrease the toxin loading. HSA, for example, has approximately 10–25 amino groups on lysine residues available to accept toxin and ligand molecules, and the human α1-acid glycoprotein can provide up to 50 lysine residues for toxin linking.

As would be understood by one of ordinary skill in the art, when the toxin complex of the present invention is provided to an individual, it may be in a composition which may contain pharmaceutically acceptable excipients such as salts, buffers, adjuvants, or other substances which are desirable for improving the efficacy of the composition or aid in its mode of administration. A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient, for example, an amount which is non toxic or minimally toxic to cells that lack cell surface receptor, but is toxic to those cells that possess the receptor and internalize the toxin complex. Generally, the dosage needed to provide an effective amount of the composition will vary depending upon such factors as the potency of the drug, an animal's or human's age, condition, sex, and extent of disease, if any, and other variables which can be adjusted by one of ordinary skill in the art.

The therapeutic compositions of the toxin complexes can be administered parenterally by injection, rapid infusion, nasopharyngeal absorption (intranasopharangeally), dermoabsorption, or orally. The compositions may alternatively be administered intramuscularly, or, preferably, intravenously.

The toxin complexes of the invention can be administered by single or multiple dosages or by continuous infusion of an effective amount. Many different techniques exist for the timing of the administering the complex when a multiple administration regimen is utilized. It is possible to use the compositions of the invention more than once to increase the levels of efficacy and to vary the type of toxin complex used. It is possible that as result of treatment, the patient may produce antibodies against a component of the toxin complex. However, by the successive use of a number of toxin complexes (e.g, varying toxin on a ligand), the neutralizing effect of antibodies to different toxins can be avoided. For example, should a patient treated with ricin A linked to a-gal epitope develop antibodies to ricin A, the patient can be further treated with an a-gal-toxin complex containing diphtheria toxin.

Having now generally described the invention, the same will be more readily understood through reference to the following examples which are provided by way of illustration, and are not intended to be limiting of the present invention, unless specified.

EXAMPLES

Example 1

Preparation of Anti-Gal-HSA Coupled to Ricin A

To a solution of α-gal-HSA (10 mg) in borate buffer (0.05 sodium borate, pH 9.0, containing 1.7% w/v NaCl) at a volume of 2.67 mL, SMPT is added (267 μL; 0.48 mg/mL) in dry dimethylformamide (DMF). The DMF is used at 10% v/v to keep the SMPT soluble. This solution is stirred for 1 h at room temperature, during which time, the succinmidyl portion of the coupling agent forms covalent bonds with the amino groups of the lysines within the human serum albumin molecule. The solution mixture is applied to a column (30×1.6 cm) of Sephadex G25 (fine). The α-gal-HSA with the linked agent is isolated in the void volume and mixed with 20 mg of Ricin A (Sigma Chemicals, St. Louis Mo.). The mixture is incubated for 72 h at room temperature under nitrogen blanket. Under these conditions the thiol group of Ricin A form s stable covalent disulfide bonds with the coupling agent.

The mixture is applied to a 2 mL of *Griffonia simplicifolia*-Sepharose,(Vector Laboratories Burlingame Calif.) that binds the α-gal-HSA-Ricin complex by interaction with this lectin. The α-Gal-toxin complex is eluted by 0.1 M α-methylgalactoside and dialyzed to remove the free carbohydrate. The efficacy of the coupling reaction is determined using SDS polyacrylamide gel electrophoresis, and staining of the separated proteins with Coummassie blue.

Example 2

Coupling Ligands to a Carrier: α1-acid Glycoprotein and α-gal

α-Gal epitopes are incorporated onto α1-acid glycoprotein according the method described in U.S. Pat. No. 5,879,675 and the procedure of LaTemple et al. (LaTemple et al., 1996, Cancer Research 56:3069–3074) (the disclosures of which are incorporated herein by reference.) Briefly, α1-acid glycoprotein is incubated in 0.05 N sulfuric acid for 2 h at 80° C. to cleave sialic acid and expose the penultimate N-acetyllactosamine (Galβ-4GlcNAc-R). The acid is removed by dialysis. The protein is incubated at 1–100 mg/mL with recombinant α1,3 galactosyltransferase (α1,3GT) and 1–20 mM UDP-Gal (uridine diphosphate-galactose) as the sugar donor. The product, α-gal-α1-acid glycoprotein, is purified by affinity chromatography on a column with the lectin *Griffonia simplicifoia I* as described in Example 1. The incorporation of α-gal epitopes onto the glycoprotein is verified by SDS polyacrylamide gel separation followed by Western blot of the glycoprotein and immunostaining with anti-Gal antibody. This carrier can then be coupled to a toxin according to, for example, the method of Example 1.

Example 3

Specific Interaction of α-gal Epitopes Complexed to Proteins with Anti-Gal Producing B Lymphocytes The specific interaction between α-gal toxin complexes and anti-Gal producing B lymphocytes is inferred from the observed specific binding of bovine serum albumin with α-gal epitopes (termed here α-gal-BSA) to such B lymphocytes. These B lymphocytes originate from the experimental animal model of knock out (KO) mice for the α1,3galactosyltransferase gene (termed here, KO mice). The cell surface carbohydrate make-up in these mice is similar to that in humans in that the mice lack α-gal epitopes because the α1,3galactosyltransferase gene was disrupted in their genome (Thall et al., 1995, J. Biol. Chem. 270: 21437). These mice can be induced to produce anti-Gal by immunization with pig kidney membranes.

Briefly, KO mice were immunized three times (each in two week intervals) with 100 mg of pig kidney membranes. The activity of the anti-Gal IgG antibody in the serum of these mice is detected by an ELISA assay at serum dilutions >1:10,000, whereas non-immunized mice have very low activity even at a serum dilution of 1:100, as shown in FIG. 2. The ELISA assay used for measuring anti-Gal activity was described in detail in the study of LaTemple and Galili (LaTemple et al., 1998, Xenotransplantation 5: 191).

The production of anti-Gal in the immunized KO mice was associated with the presence of relatively large proportions of B lymphocytes that could specifically interact with α-gal epitopes, i.e., lymphocytes with cell surface anti-Gal molecules as B cell receptors for this epitope. These lymphocytes originating from the spleen could be identified by double staining flow cytometry with the fluorescent activated cell sorter (FACS) instrument. The anti-Gal B cell receptors (i.e., cell surface immunoglobulins) on B lymphocytes were identified by their ability to bind biotinylated α-gal-BSA followed by the binding of fluorescein(FITC)-avidin to the biotin on the cell bound biotinylated α-gal-BSA, and detection of the emitted green light in the cell sorter (FIG. 3). In parallel, cells were identified as B lymphocytes by staining of the surface immunoglobulins with anti-mouse immunoglobulin antibodies coupled to phycoerythrin (PE) and detection of the emitted red color in the cell sorter. As shown in FIG. 3 non-immunized mice had almost no B lymphocytes with anti-Gal B cell receptors. However, after immunization with pig kidney membranes the proportion of these cells increased to approximately 5% of the spleen lymphocytes.

The B lymphocytes that bound biotinylated α-gal-BSA were indeed lymphocytes that are capable of producing anti-Gal. This could be demonstrated by the ELISPOT assay (FIG. 4). This assay, which is similar to the ELISA assay, identifies individual B lymphocytes that produce anti-Gal (Yang et al., 1998, J. Exp. Med. 187: 1335). Membranes in microtiter wells of ELISPOT plates (Millipore Inc.) were coated with α-gal-BSA. Subsequently lymphocytes were incubated for 24 hr in the wells at 37° C. At the end of incubation the wells were washed, incubated with horse raddish peroxidase conjugated anti-mouse immunoglobulin and the color was then developed with diaminobenzidine (DAB). Each anti-Gal producing cell was subsequently identified by the color spot formed where it secreted anti-Gal that bound to the α-gal-BSA on the membrane (FIG. 5). Magnetic beads coated with α-gal epitopes were used in order to determine association between the ability of B lymphocytes to interact with α-gal epitopes and the production of anti-Gal by these cells. For this purpose, commercially available magnetic beads coated with avidin (Dynal Inc.) were further coated with biotinylated α-gal-BSA that bound strongly to the avidin on the beads. Subsequently, these beads were washed and incubated in rotating tubes, for 4 hr at 4° C., with spleen lymphocytes from mice that were immunized with kidney membranes. This incubation enabled lymphocytes with anti-Gal B cell receptors to interact with the α-gal epitopes on the beads. At the end of incubation the beads with the lymphocytes that adhered to them were separated from the lymphocytes that did not bind to the beads by the use of a magnet. The lymphocytes of the two populations (i.e., those that adhered to the beads coated with α-gal epitopes and those that did not adhere to these beads), were plated at several concentrations in ELISPOT wells that were precoated with either α-gal-BSA, or with BSA. After 24 hr at 37° C. the plates were washed and stained for the identification of lymphocytes producing anti-Gal. The number of lymphocytes secreting anti-BSA antibodies was determined in ELISPOT wells coated with BSA and was subtracted from the number of antibody secreting lymphocytes in wells coated with α-gal-BSA. As shown in FIG. 4, lymphocyte populations that interacted with α-gal epitopes on the beads contained many more anti-Gal producing cells than lymphocytes that did not interact with this epitope on the magnetic beads. As seen in FIG. 5, the number of anti-Gal secreting lymphocytes, which is reflected by the number of spots, is many fold higher in the population of lymphocytes binding the beads than in the population that does not bind to the beads. The binding lymphocytes indeed secrete anti-Gal since almost no spots were observed when the antigen in the ELISPOT wells was BSA instead of α-gal-BSA.

These findings clearly indicate that B lymphocytes that interact with α-gal epitopes, are anti-Gal producing lymphocytes. Thus, similar binding of α-gal-toxin complexes to these lymphocytes and the subsequent internalization of these complexes can result in the elimination of the lymphocyte population that is capable of producing anti-Gal.

Example 4

Treatment of Xenograft Recipients for the Prevention of Anti-Gal Production

Patients being transplanted with a xenograft, are first depleted of circulating anti-Gal by plasmapheresis, or affinity chromatography of the plasma on columns with α-gal epitopes (Kozlowski et al., 1998, Xenotransplantation 5:122; Xu et al., 1998, Transplantation 65:172) to avoid the interaction between the α-gal-toxin complexes and anti-Gal molecules circulating in the blood. Subsequently, the α-gal-toxin complex is infused into the patient at a therapeutically effective amount. The α-gal toxin complex interacts specifically with B cell receptors on anti-Gal producing B lymphocytes. As a result of this interaction the α-gal-toxin complex is internalized into these lymphocytes and induces their death. Administration of the α-gal-toxin complex to the graft recipient continues following the transplantation of the xenograft. This results in the elimination of B lymphocyte clones that expand in response to the antigenic stimulation by α-gal epitopes on the xenograft. Ultimately, this treatment prevents anti-Gal production and may help in establishing immune tolerance to α-gal epitopes in xenograft recipients.

Example 5

Treatment for Autoimmune Disease: Systemic Lupus Erythematosus (SLE)

The anti-DNA antibodies are removed from the patient's plasma by plasmapheresis or a by adsorption on a column with coupled DNA. Subsequently, a DNA-Ricin A complex is administered to the patient. The complex binds specifically to B cells with membrane bound anti-DNA a antibodies as B cell receptors. Following this binding, the complex molecules are internalized in these B cells and induce their specific death. This results in the prevention of anti-DNA antibody production in the SLE patients.

Example 6

Treatment of Autoimmune Disease: Graves Disease

In this autoimmune disease, antibodies to thyroid stimulating hormone receptor (TSHR, also termed thyrotropin receptor) continuously stimulate the thyroid gland to produce increased amounts of thyroglobulin and of the thyroid hormones T3 and T4. The anti-TSHR antibody production can be prevented by administering to a patient a therapeutically effective amount of the toxin complex of TSHR coupled to ricin A. The human TSHR has been cloned (Libert et al., 1989, Biochem Biophys Res Comm, 165:1250) and can be produced as a recombinant protein by the same methods used for the production of recombinant α1,3 galactosyltransferase. The recombinant TSHR is purified and coupled to Ricin A or to other toxins as described above. Prior to the treatment, anti-TSHR antibodies are removed from the patients plasma by plasmapheresis or adsorption on an affinity chromatography column coupled with TSHR. Subsequently, TSHR-ricin A complex is administered to the patient. These molecules bind to B cells with membrane bound anti-TSHR antibody molecules as B cell receptors. The complex molecules are internalized and induce the death of lymphocytes that are capable of producing anti TSHR.

The invention may be embodied in other specific form without departing from the spirit or essential characteristics thereof. The present embodiments are therefore to be considered illustrative and not restrictive, the scope of the invention being dictated by the appended claims rather than by the foregoing description, and all changes which come within the meaning and range of equivalency of the claims are therefore intended to be embraced therein.

I claim:

1. A complex for the selective destruction of a B lymphocyte cell of a population of target B lymphocyte cells, comprising:

(a) a cytotoxic agent; and (b) a carrier associated with the cytotoxic agent, (i) wherein said carrier is human α1-acid-glycoprotein having carbohydrate chains modified to display α gal epitopes displayed on non-human mammalian cells, wherein said epitopes bind to antigen binding sites present on the target B lymphocyte cells.

2. The complex of claim 1 wherein the cytotoxic agent is a radioisotope.

3. The complex of claim 1 wherein the cytotoxic agent is selected from the group consisting of Ricin A, Diphtheria toxin, Pseudomonas exotoxin A, Abrin, gelonin, pokeweed antiviral protein, and saporin.

4. The complex of claim 1 wherein (a) the target cells are B lymphocytes that produce anti-gal antibodies, and (b) the antigen binding sites are anti-Gal B cell receptors.

5. The complex of claim 1 produced by the steps of:

a) enzymatically producing—gal epitopes on the carbohydrate chains of 1-acid-glycoprotein to form the carrier; and b) coupling the cytotoxic agent to the carrier.

6. The complex of claim 5 wherein the enzymatic step further includes the steps of:

(i) treating the α1-acid-glycoprotein with an agent that exposes a plurality of N-acetyllactosamine residues on the α1-acid-glycoprotein; and (ii) incubating the α1-acid-glycoprotein produced in step (i) with α1,3 galactotransferase and uridine diphosphate galactose to produce α1,3 gal epitopes on the α1-acid-glycoprotein.

7. The complex of claim 6 wherein the agent capable of exposing a plurality of N-acetyllactosamine residues is neuraminidase.

8. The complex according to claim 1 wherein the association between the carrier and the cytotoxic agent is a physical association.

9. The complex according to claim 1 wherein the association between the carrier and the cytotoxic agent is by a chemical bond.

10. The complex according to claim 9 wherein the chemical bond is a covalent bond.

* * * * *

UNITED STATES PATENT AND TRADEMARK OFFICE
CERTIFICATE OF CORRECTION

PATENT NO.     : 6,613,330 B1
DATED          : September 2, 2003
INVENTOR(S)    : Uri Galili It is certified that error appears in the above-identified patent and that said Letters Patent is hereby corrected as shown below:

<u>Title page,</u>
Item [73], Assignee, should read -- Rush University Medical Center, Chicago, IL (US) --

Signed and Sealed this

Twenty-seventh Day of January, 2004

JON W. DUDAS
*Acting Director of the United States Patent and Trademark Office*